US008182503B2

(12) United States Patent
Takashima

(10) Patent No.: US 8,182,503 B2
(45) Date of Patent: May 22, 2012

(54) PROSTATE MASSAGE APPARATUS

(76) Inventor: Jiro Takashima, Houston, TX (US)

( * ) Notice: Subject to any disclaimer, the term of this patent is extended or adjusted under 35 U.S.C. 154(b) by 713 days.

(21) Appl. No.: 12/041,501

(22) Filed: Mar. 3, 2008

(65) Prior Publication Data

US 2009/0222034 A1 Sep. 3, 2009

(51) Int. Cl.
*A61M 29/00* (2006.01)

(52) U.S. Cl. .................................................... 606/197

(58) Field of Classification Search .................. 606/191, 606/196, 197, 234–236; 128/61, 62; 601/136, 601/137
See application file for complete search history.

(56) References Cited

U.S. PATENT DOCUMENTS

| | | | | |
|---|---|---|---|---|
| 1,278,944 | A * | 9/1918 | Landis | 606/197 |
| 5,797,950 | A * | 8/1998 | Takashima | 606/197 |
| 7,214,239 | B2 * | 5/2007 | Chen | 606/236 |

FOREIGN PATENT DOCUMENTS

WO WO 2007/012792 1/2007

OTHER PUBLICATIONS

EPO Communication (Office Action) issued Feb. 23, 2010, by the European Patent Office in related European Patent Application No. EP-09153839.7 (3 pages) (Note: The European Search Report referenced therein was previously filed with the USPTO in the Supplemental IDS filed on Apr. 28, 2009.).
First Office Action issued Jul. 9, 2010, by the State Intellectual Property Office of People's Republic of China, in related Chinese Patent Application No. 200910118252.3, with English translation (8 pages).
European Search Report issued Apr. 9, 2009, by the European Patent Office (20 pages).
Third Office Action issued Apr. 20, 2011, by the China Patent Office in related Chinese Patent Application No. 200910118252.3, with English translation (7 pages).

* cited by examiner

*Primary Examiner* — Kevin T Truong
(74) *Attorney, Agent, or Firm* — Osha · Liang LLP

(57) ABSTRACT

An apparatus for massaging a prostate includes a body having a substantially ellipsoid shape and sized to fit in a rectum through a sphincter, wherein the body comprises a head portion and a neck portion, wherein the head portion is configured to contact the prostate through the rectum wall when inserted in the rectum, and wherein the neck portion has a tapered section with gradually reducing diameters distal to the head portion; and a retainer bar joined the body at one end of the neck portion to form a substantially T-shaped structure, wherein the retainer bar comprises two contact points for contacting a first acupressure point, which is located in the perineum region between the anus and the scrotum, and a second acupressure point, which is located about midway between the anus and the lower end of the coccyx.

20 Claims, 7 Drawing Sheets

PROSTATE MASSAGE APPARATUS

BACKGROUND OF INVENTION

1. Field of the Invention

The present invention relates to apparatus for preventing and treating prostate abnormalities, including benign prostate hyperplasia (BPH) and prostatitis. More particularly, the present invention relates to devices for massaging the prostate gland.

2. Background Art

Prostate is a compound tubuloalveolar exocrine glad that is part of the male reproduction system in mammals. Common prostate abnormalities include benign prostate hyperplasia (BPH), prostatitis, and prostate cancer. BPH is a condition with enlarged prostate gland, often occurs in older men. Severe BPH can cause urination difficulties due to the enlarged prostate pressing against the urethra. BPH can be treated with medication or with surgery that removes part of the prostate.

Prostatitis is inflammation of the prostate gland. There are different forms of prostatitis. Acute prostatitis and chronic bacterial prostatitis may be treated with antibiotics, while chronic non-bacterial prostatitis, which accounts for about 95% of prostatitis diagnoses, may be treated with a variety of modalities, including α-adrenergic blockers, physical therapy, psychotherapy, and antihistamines.

Chronic non-bacterial prostatitis may lead to fluid build up in the prostate, resulting in a congested prostate. One treatment for chronic non-bacterial prostatitis is the prostate massage. Some urologists believe that the most effective treatment for such prostatitis is for the doctor to massage the prostate at regular intervals. However, such massages can be difficult to obtain because it often requires frequent visits by the patients to doctor's offices, which is associated with considerable expense and inconvenience. Therefore, there is a need for devices that would allow an individual to carry out his own prostatic massage.

Since prostate is located proximate the anus, various devices that can contact prostate gland through rectal wall have been devised in the art. For example, U.S. Pat. No. 4,542,753, issued to Brenman et al., discloses an apparatus having electrodes and circuitry for generating electrical signals to stimulate prostate gland and erectile tissue, after the device is disposed in the rectum.

U.S. Pat. No. 5,404,881, issued to Cathaud et al., describes a trans-rectal probe made of a flexible self-supporting polymer material. The flexibility of the polymer material enables it to comply with the shape therein, making it possible to achieve safe and reliable positioning of an instrument for detection or therapeutic treatment of an organ (such as prostate) through the rectum.

U.S. Pat. No. 2,478,786, issued to H. M. Smallen, describes a prostate gland massaging implement that is operated by hand. This implement includes a lever having an interior handle which constitutes a power arm to extend down in front of the abdomen and a substantially horizontal portion extending under the groin and offset laterally to avoid the genital organs. The implement has an upwardly and forwardly bent posterior portion which forms the work arm. This work arm extends into the rectal passage to bear against the frontal wall thereof adjacent the prostate gland. The bent portion between the horizontal and the posterior portions serves as a fulcrum point against the front wall of the rectal opening when the implement is subject to pivotal movement around this point.

The inventor of the present application has invented several prostate massaging devices, as disclosed in U.S. Pat. Nos. 5,797,950; 5,861,000; 6,589,193; 6,802,850; and 7,211,059; and published U.S. Patent Application Nos. 2002/0040200; 2004/0158182; and 2005/0266048. These patents and applications are incorporated by reference in their entirety. These devices are operated by the contraction of the sphincter muscles, without the need of hand operations. FIGS. 1 and 2 illustrate two of such devices.

As shown in FIG. 1, a device for prostate massage has a generally rod-shape body comprising a head portion 112 designed to contact the prostate through the rectum, a neck portion 123, and a retainer portion 114. The neck portion 123, having gradually reducing diameters from the head portion 112, is designed to allow contraction of the sphincter muscle to push the device upward to massage the prostate. The retainer portion 114, which joins the neck portion 123 at the bend 121 to form a generally C-shape, is designed to prevent the device from completely slipping into the rectum and also to contact the perineum-groin area, thereby forcing the head portion 112 to contact the prostate.

FIGS. 2A and 2B show another prostate massaging device invented by the present inventor, illustrating the location of the device in the rectum 24 before (FIG. 2A) and after (FIG. 2B) sphincter muscle 26 contraction. As the device is pushed up by the sphincter 26 contraction, the head portion 42 presses against the prostate 28, as shown in FIG. 2B. When the sphincter muscles 26 relax, the device will slide downward, resulting in less compression of the prostate, as shown in FIG. 2A. Therefore, repeated contraction and relaxation of the sphincter muscles can produce the desired massage of the prostate without using a hand.

These prior art devices provide convenient ways to massage a congested prostate. However, there remains a need for improved prostate massage devices.

SUMMARY OF INVENTION

One aspect of the invention relates to apparatus for massaging a prostate. An apparatus in accordance with one embodiment of the invention includes a body having a substantially ellipsoid shape and sized to fit in a rectum through a sphincter, wherein the body comprises a head portion and a neck portion, wherein the head portion is configured to contact the prostate through the rectum wall when inserted in the rectum, and wherein the neck portion has a tapered section with gradually reducing diameters distal to the head portion; and a retainer bar joined the body at one end of the neck portion to form a substantially T-shaped structure, wherein the retainer bar comprises two contact points for contacting a first acupressure point, which is located in the perineum region between the anus and the scrotum, and a second acupressure point, which is located about midway between the anus and the lower end of the coccyx, wherein the head portion and the two contact points are configured such that they can contact the prostate, the first acupressure point, and the second acupressure point simultaneously.

Another aspect of the invention relates to methods for massaging a prostate. A method in accordance with one embodiment of the invention includes providing a device configured to contact the prostate, a first acupressure point located in the perineum region between the anus and the scrotum, and a second acupressure point located about midway between the anus and the lower end of the coccyx; inserting the device into the rectum, wherein the device when inserted into the rectum has a tapered section contacting sphincter muscles; contracting the sphincter muscles to move the device upward thereby the device massages the prostate and applies pressure to the first acupressure point and the second acupressure point.

Other aspects and advantages of the invention will be apparent from the following description and the appended claims.

DETAILED DESCRIPTION

Embodiments of the invention relates to prostate massage apparatus that rely on sphincter muscles to provide the massage action, i.e., converting the sphincter's contraction and relaxation actions to an up-and-down motion of the device in the rectum to massage the prostate. In addition, the apparatus in accordance with embodiments of the invention can provide pressure in the perineum region and a region midway between the anus and the lower end of the coccyx (tail bone) to produce acupressure therapeutic effects to stimulate these areas for therapeutic purposes. Embodiments of the invention are based on unexpected findings that pressuring the two acupressure points while massaging the prostate can provide improved user experience. Specifically, compression at these two acupressure points while massaging the prostate was unexpectedly found to provide comfortable and pleasant feelings to the users. The pleasant feelings will encourage the use of the devices and therefore promote patient compliance.

Acupuncture is gradually gaining acceptance around the world for its medical benefits, particularly in the relief and management of pains. World Health Organization (WHO) has published a uniform, standardized nomenclature for acupuncture, "Standard acupuncture nomenclature," Second edition, 1993 (ISBN 9290611057).

Figure 8:
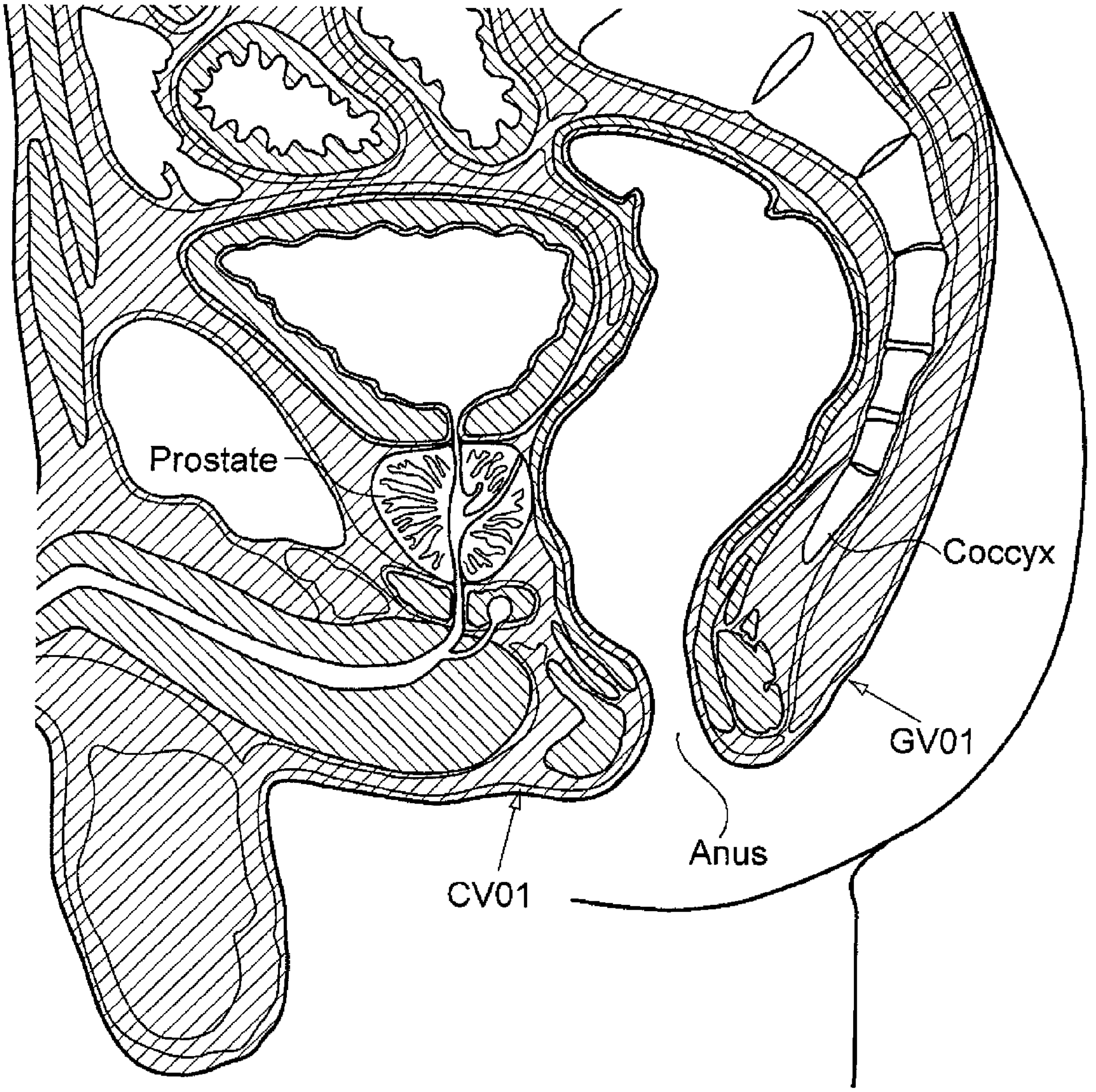
FIG. 8 shows an illustration of a sectional view of a lower portion of a human body, illustrating the locations of the two acupressure points.

The perineum region includes the CV1 acupoint (Chinese name: Huiyin; Japanese name: Ein; Wade-Gilles name: Hui Yin), which is located between the anus and the scrotum, as shown in FIG. 8. CV1 acupoint is the first acupoint along the Conception Vessel Meridian. In acupuncture, CV1 is for the treatment of various genitourinary disorders, hemorrhoid conditions, and rectal prolapse. Thus, applying acupressure to the perineum region may provide therapeutic benefits.

The region about midway between the anus and the tip of coccyx includes the GV1 acupoint, as shown in FIG. 8. This region will be referred to as the "GV1 region" in the following description. GV1 is the first acupoint along the Governor Vessel Meridian. Its Chinese name is "Chang Qiang" (Japanese name: Chokyo; Wade-Gilles name: Chang Chiang). In acupuncture, GV1 is for the treatment of hemorrhoid, rectal prolapse, anal fissure, and various genitourinary ailments, including urinary tract disorder, urine retention, sexual exhaustion, impotence, and seminal emission. See: http://www.yinvanghouse.com/acupuncturepoints/gv1. Thus, applying pressure to this region may provide therapeutic benefits.

Figure 3A:
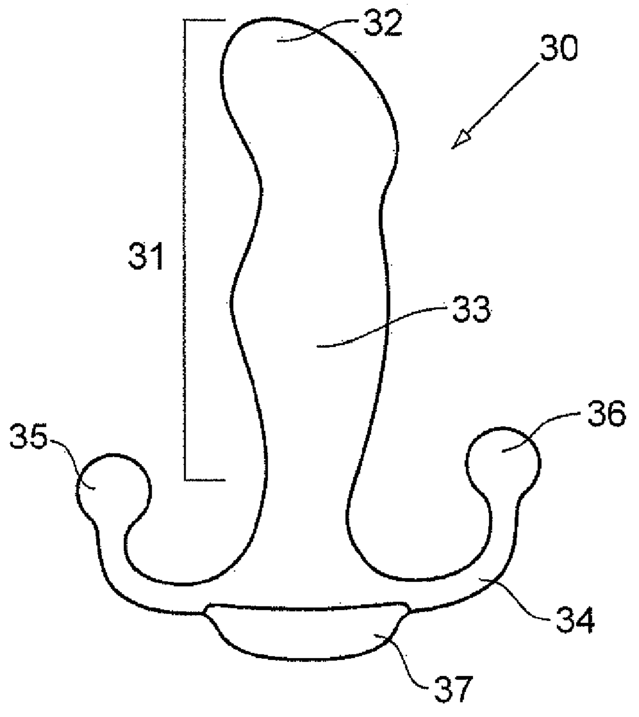
FIG. 3A shows a prostate massaging apparatus in accordance with one embodiment of the invention.

In order to massage the prostate and, at the same time, apply pressure to the perineum and the GV1 regions, apparatus in accordance with embodiments of the invention generally have a substantially T-shaped configuration. FIG. 3A shows one such example, which is displayed in an inverted-T orientation.

As shown in FIG. 3A, a prostate massage apparatus 30 in accordance with one embodiment of the invention includes a body 31 and a retainer bar 34, joined in a substantially T-shaped configuration. The T-shape configuration need not have a precise 90° joint, as illustrated by the dotted horizontal line H and vertical line V shown in FIG. 3B. In this illustration, the horizontal line H and the vertical line V are drawn passing through the longitudinal axes (the axes along the longer dimensions) of the body and the retainer bar, respectively. Preferred embodiments have the substantially T-shaped in a configuration like an "italicized" T such that the two angles formed by the body and the retainer are not rectangles. In preferred embodiments, the body 31 tilts (inclines) backward, i.e., towards knob 36 that is designed to contact the GV1 acupressure point.

Figure 3B:
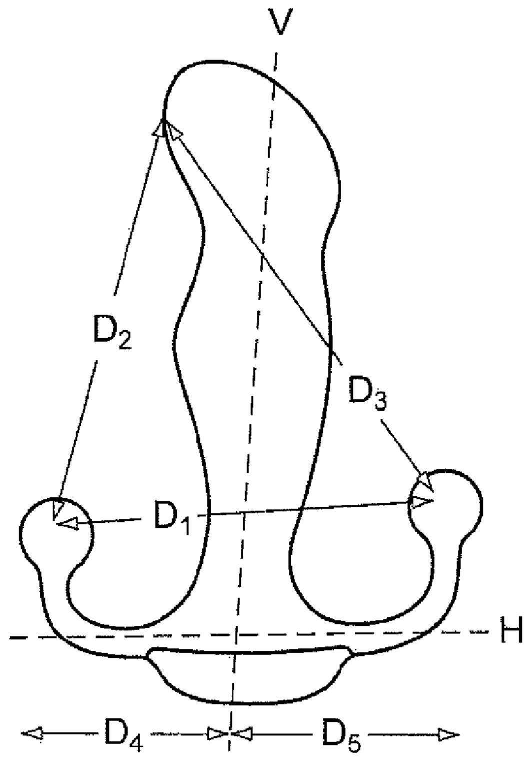
FIG. 3B shows the apparatus of FIG. 3A, illustrating the dimensions.

Referring to FIG. 3B, since a device of the invention is for massaging the prostate and applying pressures to two acupressure points, the three distances $D_1$, $D_2$, and $D_3$ shown in FIG. 3B should be properly sized to fit an individual. For an average adult, $D_1$ is about 2.5-4.5 inches (about 7-12 cm), preferably about 3 inches (about 8 cm); $D_2$ is about 2.5-5 inches (about 7-13 cm), preferably about 3.5 inches (about 9 cm); and $D_3$ is about 3-5.5 inches (about 8-14 cm), preferably about 3.75 inches (about 10 cm).

Note that the distances of the two contact points ($D_4$ and $D_5$ in FIG. 3B) on the retainer bar need not be equally spaced from the joint, where the body 31 meets the retainer 34. In addition, the two contact points 35 and 36 are at different distances from the horizontal line H that passes through the retainer 34, with the contact point 36, which is designed to pressure the GV1 region, farther off the horizontal line H.

Referring again to FIG. 3A, the body 31 of the device is generally an elongated ellipsoid, which may have bumps and/or indentations (as in the embodiment shown) to better fit the inside of a rectum or to have better prostate massage functions. The diameters of the body 31 should be sized to be inserted into a human rectum through sphincter. Typically, the largest diameter of the generally rod shaped body 31 may be about 2 inches (about 5 cm) or less, more preferably about 1.5 inch (about 4 cm) or less. The length of the body 31 should be long enough to reach the prostate, but not too much longer. Thus, the body 31 is preferably about 3-6 inches (about 8-15 cm) long (as measured from the top of the head to the joint at the retainer bar), more preferably about 4-5 inches (about 10-13 cm) long, and most preferably about 4-4.5 inches (about 10-12 cm) long.

Figure 1:
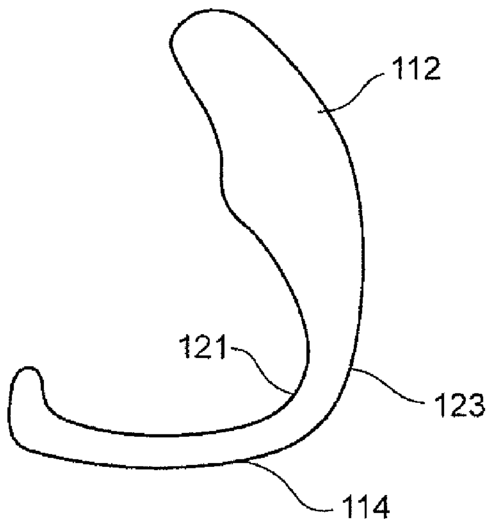
FIG. 1 shows a prior art prostate massaging apparatus.
Figure 2A:
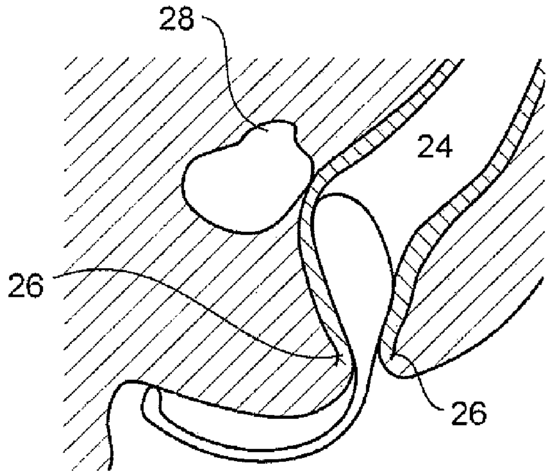
FIGS. 2A and 2B show a prior art prostate massaging apparatus in use.
Figure 2B:
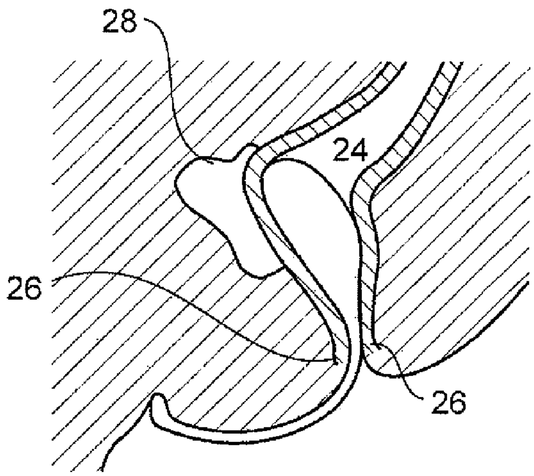

As shown in the embodiment of FIG. 3A, the body 31 of this apparatus has a head portion 32 and a neck portion 33. The head portion 32 may have a generally bulbous shape and is configured to contact the prostate (through the rectum wall). The neck portion 33 may have a generally rod or cone shape with gradually decreasing diameters (i.e., tapered) towards the joint (i.e., the diameters decrease in a direction from the head portion 32 towards the retainer bar 34). The tapered configuration of the neck portion 33 allows the contraction of the sphincter muscles to push the body 31 upward during use (as shown in FIG. 2B).

The retainer bar 34 serves to prevent the body 31 from slipping completely into the rectum or reaching too far up. In addition, in accordance with embodiments of the invention, the retainer bar 34 provides "contact points" that can apply pressures to both the perineum and the GV1 regions. In the embodiment shown in FIG. 3A, the retainer bar 34 has bent ends (the L-shaped end portions of the retainer bar 34 bend toward the body 31) that include knobs (or bulbous structures) 35 and 36 for contacting and applying pressure to the perineum and the GV1 regions, respectively.

The structural features (e.g., knobs 35, 36) that are designed to contact the perineum and GV1 regions will be referred to generally as "contact points" in this description. Note that they need not have the bulbous shape as shown in FIG. 3A. Instead, they may be in any shape, including ellipsoidal shape, cylindrical shape, cone shape, and the like. Furthermore, a "contact point" may be simply a surface or an area on the retainer bar 34 intended to contact the perineum or the GV1 region. See for example, the embodiment shown in FIG. 3C, in which the contact point 35' is simply the round end of the retainer 34', while the contact point 36' is a bulge at the end of the retainer 34'. One of ordinary skill in the art would appreciate that the "contact points" of a device of the invention may have any shape.

Figure 3C:
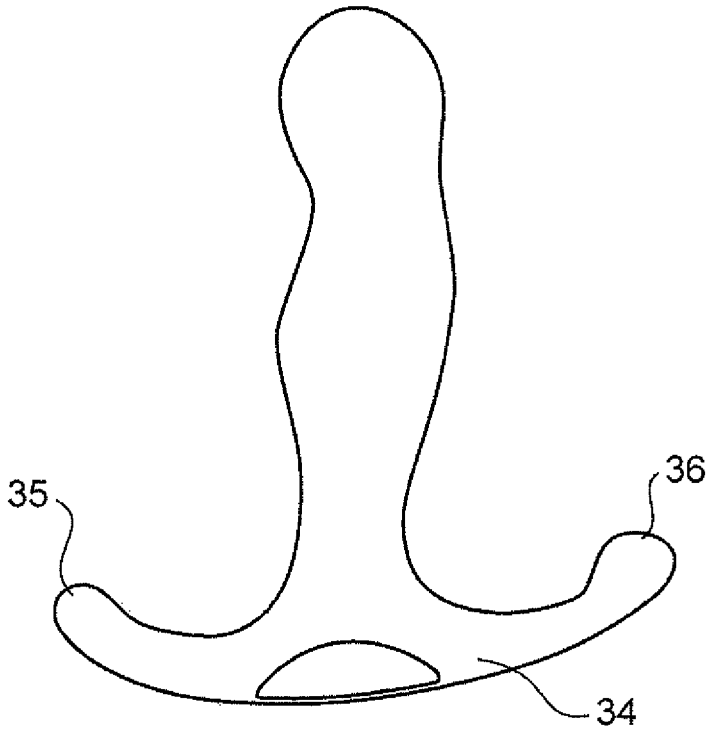
FIG. 3C illustrates another example of an apparatus of the invention, showing an example of different shapes of the retainer bars and the contact points.

In the embodiment shown in FIG. 3A, the retainer bar 34 has ends that bend towards the body 31. Note that such bent ends are not necessary for embodiments of the invention. For example, some embodiments of the invention may have the knobs 35 and 36 attached directly to the ends of the retainer bar 34 without the intervening bend sections. In other examples, the retainer 34 may have gradual curves (instead of relatively sharp bends as shown in FIG. 3A), as shown in FIG. 3C, to facilitate the application of pressures to the perineum and GV1 regions.

The embodiment shown in FIG. 3A also includes a reinforcement handle (ridge) 37 attached to the underside of the retainer bar 34 to give it more rigidity. However, in accordance with some embodiments of the invention, the retainer bar 34 may be without such a reinforcement handle 37, while some embodiments may even include retainers with some flexibility to help reduce the pressure applied at the acupressure points.

Figure 4:
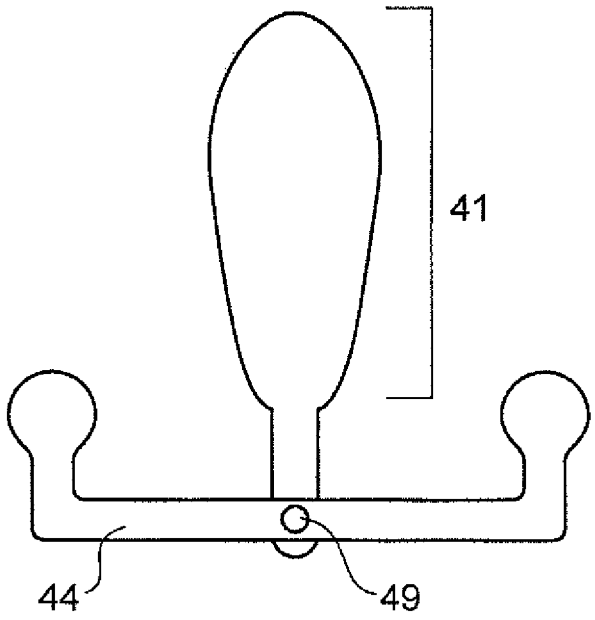
FIG. 4 shows another embodiment of the invention having a body portion flexibly joined with the retainer bar.

As noted above, embodiments of the invention allow an user to massage a prostate while pressuring two acupressure points, CV1 and GV1. Since the distances between these points may vary slightly among different individuals, some embodiments of the invention may provide some flexibilities with regard to the shape or configuration of the devices used for the massage. For example, some embodiments may provide flexibility in terms of how the body portion joins the retainer bar, as illustrated in FIG. 4. FIG. 4 shows one example of an embodiment of the invention, in which the body portion 41 and the retainer bar 44 are joined by a pivot mechanism 49 such that the body 41 may joint the retainer 44 at different angles. The pivot mechanism 49 may allow a user to select a proper angle and fix the angle during use. Alternatively, the pivot mechanism 49 may allow the joint to rotate during use, i.e., to allow some angular freedom during use. Furthermore, in some embodiments, the pivot mechanism 49 may include a mechanism that allow the body portion 41 to be adjusted up and down such that the body portion 41 is situation at different distances from the retainer bar 44. All these flexible mechanisms will be generally referred to as "flex joints," and the manner the body portion 41 joins the retainer bar 44 will be referred to as "flexibly joined."

Figure 5:
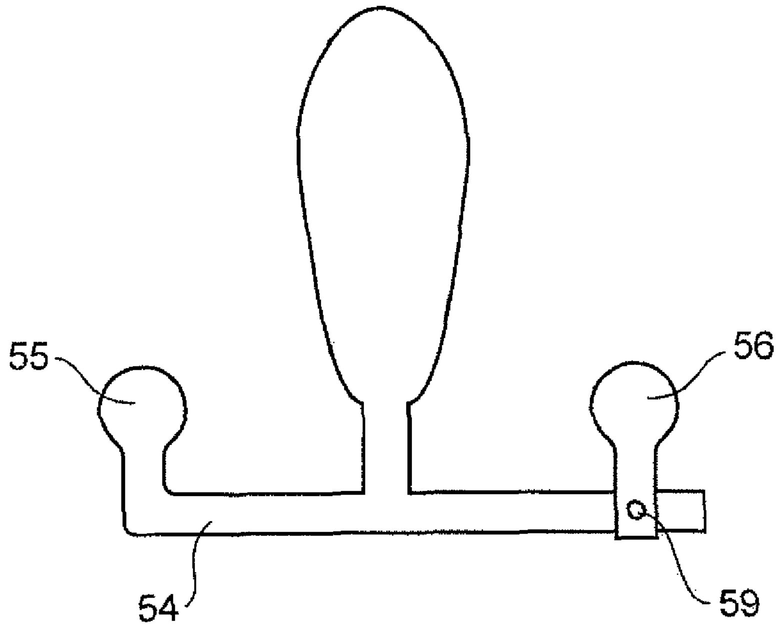
FIG. 5 shows another embodiment of the invention having one of the contact points adjustably attached to the retainer bar.

In addition to allowing flexibility at the body and retainer bar join, some embodiments of the invention may allow flexibility in the distances between the "contact points" that are designed to pressure the CV1 and GV1 acupressure points. For example, FIG. 5 shows one embodiment of the invention, in which the contact point 56 is adjustably attached to the retainer bar 54 via an adjuster mechanism 59. While in this embodiment, only the contact point 56 is shown to be "adjustably attached to" the retainer bar 54, one of ordinary skill in the art would appreciate that the other contact point 55 may also be made adjustable without departing from the scope of the invention.

Figure 6:
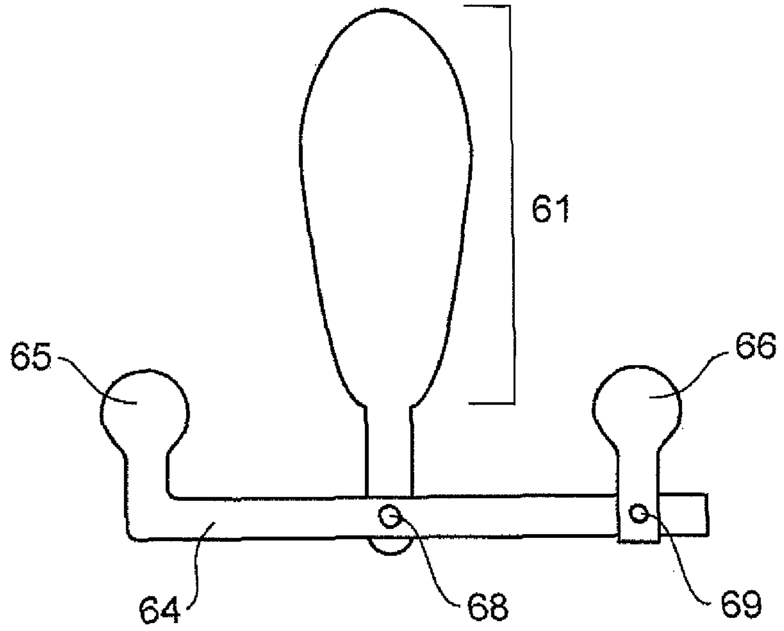
FIG. 6 shows another embodiment of the invention having one of the contact points adjustably attached to the retainer bar and the body portion flexibly jointed with the retainer bar.
Figure 7:
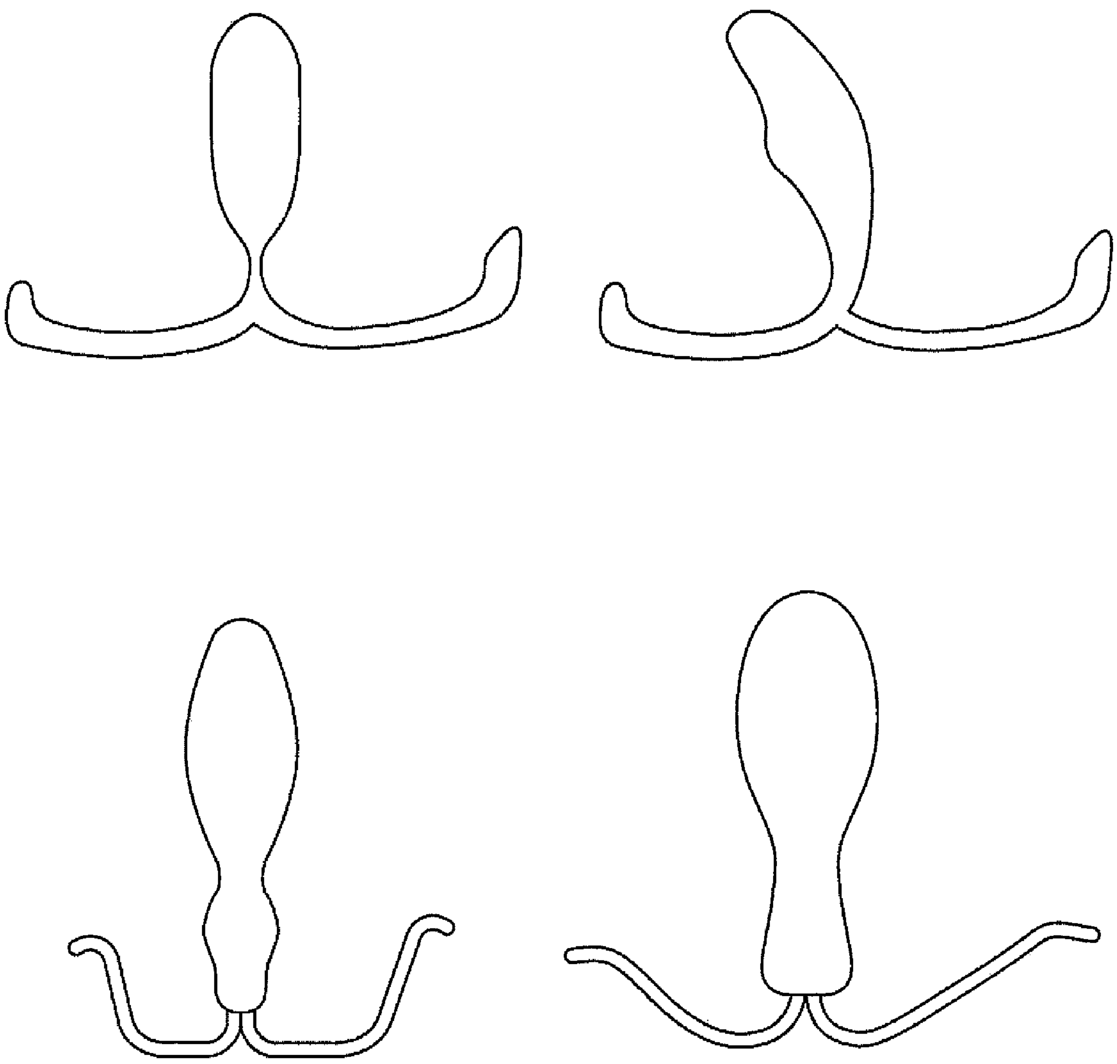
FIG. 7 shows several variations and modifications of the prostate massaging apparatus in accordance with embodiments of the invention, illustrating various shapes of the bodies and retainer bars that may be used with embodiments of the invention.

Similarly, the flexibility may be allowed both at the joint (as shown in FIG. 4) and the contact points (as shown in FIG. 5). FIG. 6 shows one embodiment of the invention, in which the body portion 61 joins the retainer bar 64 in a flexible manner via a pivot mechanism 68. At the same time, the contact point 66 is also "adjustably attached to" the retainer bar 64 by an adjuster mechanism 69. The term "adjustably attached to" means the contact points are not fixedly attached to the retainer bars.

The above examples illustrate some variations of how the body portions can be joined with the retainer bars and how the contact points can be varied. In addition, the body portions and the retainer bars of embodiments of the invention may have various shapes. For example, some possible shapes of the body portion have been disclosed in the patents and patent applications by the inventor of the present invention, as noted above. Some of these variations are illustrated in FIG. 4. Note that these examples in FIG. 4 are provided for illustration purpose only. One of ordinary skill in the art would appreciate that various modifications and variations are possible without departing from the scope of the invention.

Apparatus in accordance with embodiments of the invention may be made of any suitable materials, including plastics, polymers, rubbers, elastomers, silicon, composites, metals and alloys. An apparatus of the invention may or may not be made entirely of a single materials. For example, the head portion of the apparatus may be made of a rubber-like material, while the neck portion may be made of a rigid material, or vice versa. Alternatively, the apparatus may be made of one material in the interior (e.g., metal or alloy), while the exterior of the apparatus may be made of another material (e.g., a rubber-like material).

Figure 9:
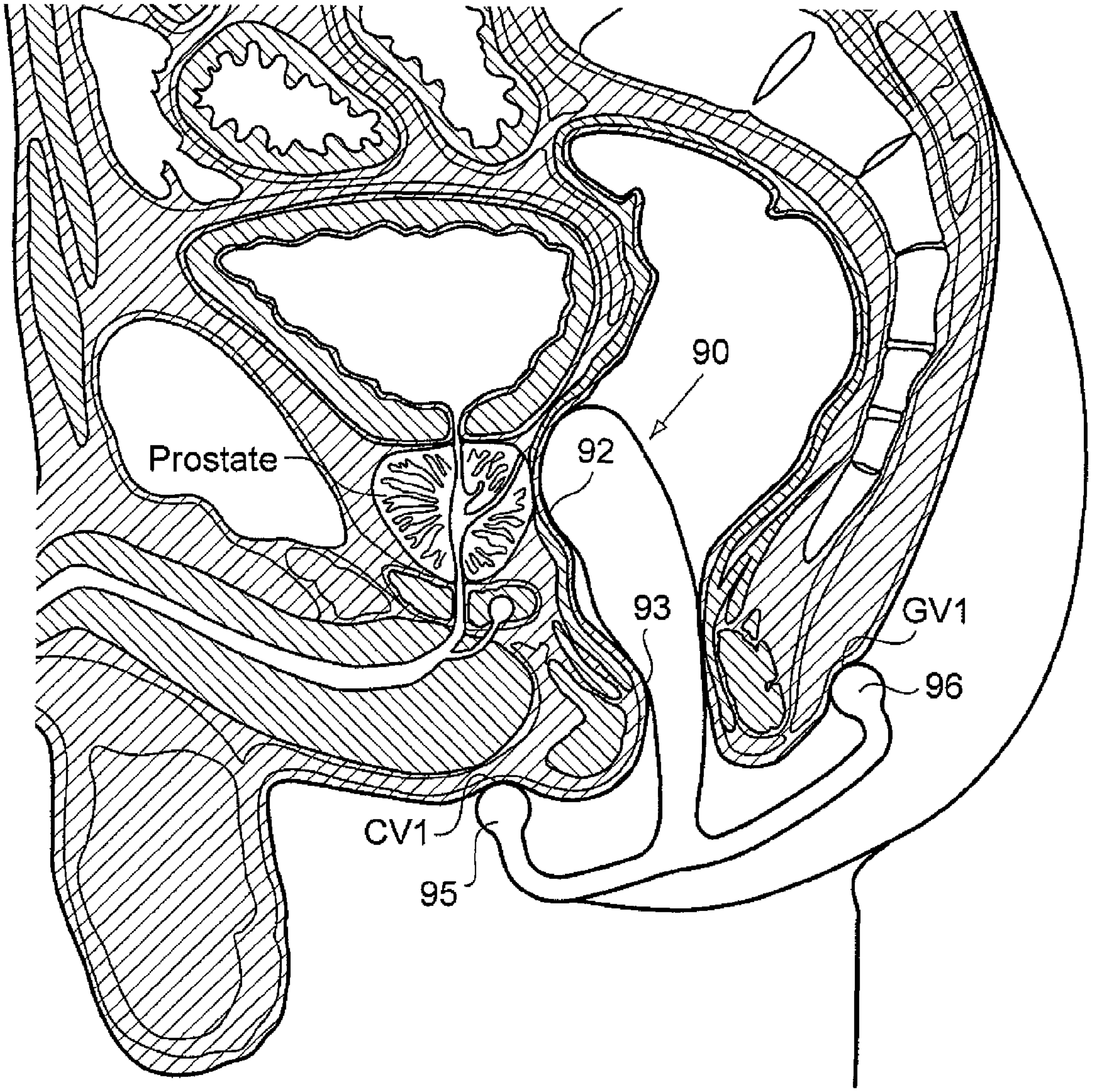
FIG. 9 shows a diagram illustrating a prostate massaging apparatus in use.

FIG. 9 shows a prostate massage device of the invention in use. As shown, the massage device 90 is inserted in a rectum, the head portion 92 of which lightly contacts the prostate through the rectum wall, while the neck portion 93 is in contact with the sphincter muscles. The contact points 95 and 96 of the device contacts the CV1 and GV1 acupressure points, respectively. When the sphincter muscles contract, the device 90 will slide up due to the tapered shape of the neck portion 93. When the device slides up, it will rub against the prostate and also put pressure on the CV1 and GV1 acupressure points. When the sphincter muscles relax, the device will slide down to its original location, as shown in FIG. 9. Thus, repeated contraction and relaxation of the sphincter muscles will result in up and down movements of the device, leading to massage of the prostate, as well as pressuring of the CV1 and GV1 acupressure points.

Advantages of the invention may include one or more of the following. A device of the invention can provide prostate massage by the user by the action of the sphincter muscles; no hand operation is needed. In addition, a device of the invention can provide pressures to the perineum and GV1 regions, while massaging the prostate. The simultaneous pressuring of these acupressure points can provide additional therapeutic benefits to the users.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An apparatus for massaging a prostate, comprising:

a body having a substantially ellipsoid shape and sized to fit in a rectum through a sphincter, wherein the body comprises a head portion and a neck portion, wherein the head portion is configured to contact the prostate through the rectum wall when inserted in the rectum, and wherein the neck portion has a tapered section with gradually reducing diameters distal to the head portion; and a retainer bar joined the body at one end of the neck portion to form a substantially T-shaped structure, wherein the retainer bar comprises two contact points for contacting a first acupressure point located in the perineum region between the anus and the scrotum, and a second acupressure point located about midway between the anus and the lower end of the coccyx, wherein the head portion and the two contact points are configured such that they can contact the prostate, the first acupressure point, and the second acupressure point simultaneously.

2. The apparatus of claim 1, wherein the retainer bar has a curved shape with the two ends of the retainer bar curved towards the body.

3. The apparatus of claim 2, wherein at least one of the two contact points comprises an end portion of the retainer bar.

4. The apparatus of claim 1, wherein at least one of the two contact points comprises a bulbous structure.

5. The apparatus of claim 1, wherein the two contact points are separated by a distance of about 3 inches.

6. The apparatus of claim 1, wherein a largest diameter on the body is no larger than about 2 inches.

7. The apparatus of claim 1, wherein a length of the body is about 3.5-5.0 inches.

8. The apparatus of claim 1, wherein the substantially T-shaped structure has a configuration that the two angles formed by the body and the retainer bar are not rectangles.

9. The apparatus of claim 1, wherein the body is flexibly joined with the retainer bar.

10. The apparatus of claim 1, wherein at least one of the two contact points is adjustably attached to the retainer bar.

11. The apparatus of claim 10, wherein the body is flexibly joined with the retainer bar.

12. The apparatus of claim 1, wherein the body and the retainer bar are made of different materials.

13. The apparatus of claim 1, wherein the retainer bar is made of a flexible material.

14. The apparatus of claim 1, the apparatus is made of a material selected from the group consisting of plastic, polymer, rubber, elastomer, silicon, composite, metal, and alloy.

15. A method for massaging a prostate, comprising:

providing a device configured to contact the prostate, a first acupressure point located in the perineum region between the anus and the scrotum, and a second acupressure point located about midway between the anus and the lower end of the coccyx;

inserting the device into the rectum, wherein the device when inserted into the rectum has a tapered section contacting sphincter muscles;

contracting the sphincter muscles to move the device upward thereby the device massages the prostate and applies pressure to the first acupressure point and the second acupressure point.

16. The method of claim 15, further comprising: relaxing the sphincter muscles to allow the device to slide downward; and re-contracting the sphincter muscles to move the device upward; and repeating the steps of relaxing and re-contracting.

17. The method of claim 15, wherein the device comprises:

a body having a substantially ellipsoid shape and sized to fit in a rectum through a sphincter, wherein the body comprises a head portion and a neck portion, wherein the head portion is configured to contact the prostate through the rectum wall when inserted in the rectum, and wherein the neck portion has a tapered section with gradually reducing diameters distal to the head portion; and a retainer bar joined the body at one end of the neck portion to form a substantially T-shaped structure, wherein the retainer bar comprises two contact points for contacting a first acupressure point located in the perineum region between the anus and the scrotum, and a second acupressure point located about midway between the anus and the lower end of the coccyx, wherein the head portion and the two contact points are configured such that they can contact the prostate, the first acupressure point, and the second acupressure point simultaneously.

18. The method of claim 17, wherein the body is flexibly joined with the retainer bar.

19. The method of claim 17, wherein at least one of the two contact points is adjustably attached to the retainer bar.

20. The method of claim 17, wherein at least one of the two contact points comprises a bulbous structure.

* * * * *